(12) United States Patent
Sadegh et al.

(10) Patent No.: US 7,204,160 B1
(45) Date of Patent: Apr. 17, 2007

(54) BIAXIAL AND SHEAR TESTING APPARATUS WITH FORCE CONTROLS

(75) Inventors: Ali M. Sadegh, Franklin Lakes, NJ (US); Paul V. Cavallaro, Rayhnam, MA (US); Claudia J. Quigley, Lexington, MA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 11/401,014

(22) Filed: Mar. 30, 2006

Related U.S. Application Data

(63) Continuation-in-part of application No. 10/905,076, filed on Dec. 14, 2004, now Pat. No. 7,051,600, which is a continuation-in-part of application No. 10/851,748, filed on May 24, 2004, now Pat. No. 6,860,156.

(51) Int. Cl.
*G01D 7/00* (2006.01)
(52) U.S. Cl. .............................................. 73/862.041
(58) Field of Classification Search ............ 73/862.041
See application file for complete search history.

(56) References Cited

U.S. PATENT DOCUMENTS

| | | | |
|---|---|---|---|
| 3,776,028 A | 12/1973 | Lynch et al. | |
| 4,192,194 A | 3/1980 | Holt | |
| 4,885,941 A | 12/1989 | Vardoulakis et al. | |
| 5,005,424 A * | 4/1991 | Markowski | 73/834 |
| 5,144,844 A | 9/1992 | Mathiak et al. | |
| 5,279,166 A | 1/1994 | Ward et al. | |
| 5,448,918 A | 9/1995 | Tucchio | |
| 5,905,205 A | 5/1999 | Clay | |
| 6,860,156 B1 | 3/2005 | Cavallaro et al. | |
| 6,951,144 B2 * | 10/2005 | Mansky | 73/862.046 |

* cited by examiner

*Primary Examiner*—Michael Cygan
*Assistant Examiner*—O. Davis
(74) *Attorney, Agent, or Firm*—James M. Kasischke; Michael P. Stanley; Jean-Paul A. Nasser

(57) ABSTRACT

A testing apparatus having four-bar linkages pivotable to sleeves on opposite vertices with the sleeves of each vertex rotationally attached to each other. Links of each linkage are pivotally attached to loading plate assemblies securing a test specimen. During loading, the assemblies move toward or away from each other; thereby, applying compression or tension to the specimen. A pressure system fluidly impacts opposite faces of a piston of the assembly such that one of the faces is pressurized and impacts arms of the assembly for a sliding motion to move toward or away from the longitudinal axis of the apparatus thereby, applying a compression or tensile load on the specimen or augmenting the loads applied by the movement of the loading plate assemblies. The pressure system includes a controller connected to a reservoir, a pressurized source, a plurality of shutoff valves and pressure-adjustable check valves.

16 Claims, 15 Drawing Sheets

BIAXIAL AND SHEAR TESTING APPARATUS WITH FORCE CONTROLS

CROSS-REFERENCE TO RELATED APPLICATIONS

This application is a continuation-in-part of and claims the benefit of U.S. patent application Ser. No. 10/905,076—filed on Dec. 14, 2004 now U.S. Pat. No. 7,051,600 and allowed on Dec. 30, 2005, entitled "Triaxial Tension Compression, Shear Testing Apparatus" which is a continuation-in-part of and claims the benefit of U.S. patent application Ser. No. 10/851,748—filed on May 24, 2004 and issued on Mar. 1, 2005 as U.S. Pat. No. 6,860,156, entitled "Combined In-Plane Shear and Multi-Axial Tension or Compression Testing".

STATEMENT OF GOVERNMENT INTEREST

The invention described herein may be manufactured and used by or for the Government of the United States of America for governmental purposes without the payment of any royalties thereon or therefor.

BACKGROUND OF INVENTION (1) Field of the Invention

The present invention relates to a combined in-plane shear and biaxial tension or compression loading apparatus, having hydraulic or pneumatic force controls to independently control the loading along, varying axis of a test specimen, for testing mechanical properties of metals, plastics, composites, woods, fabrics, elastomers, and other materials as the test specimen.

(2) Description of the Prior Art

It is known in the art that pressurized fabric tubes; pressure-stabilized beams (also known as air beams) and air-inflated structures are practical fixtures for lightweight and rapidly deployable structures such as temporary shelters, tents, temporary bridges and space structures. Presently, plain-woven fabrics have been utilized in air-inflated structures. As such, design optimization of an air-inflated structure depends on a thorough understanding of woven fabric mechanics.

Furthermore, the advent of structural fiber materials and weaving/braiding technologies has improved the load carrying capacity of pressurized fabric structures. Accordingly, there has been increasing interest in modeling the mechanical behavior of woven fabrics. However, this class of materials has complex microstructures that lead to complex mechanical responses. In particular, the mechanical characteristics of plain-woven fabrics used in inflated structures exhibit high non-linearity with dependence on the internal pressure and contact interactions within the woven fabric.

Therefore, there is a need for a testing apparatus, which allows the measurement of the elastic and shear moduli for air beams since induced inflation pressure creates a biaxial loading in fabric. To measure the shear moduli of the fabric, an in-plane shear loading is needed. Specifically, there is a need for a testing apparatus capable of applying combined in-plane shear load and biaxial tensile load. There is a further need that the test apparatus be capable of loading non-orthogonal composite or fabric materials with equi-biaxial or non-equi biaxial loading.

Biaxial testing apparatuses or in-plane shear testing apparatuses are known in the art; however, none of the apparatuses have a combined feature of in-plane shear and compression/tension testing capabilities. Furthermore, none of the apparatuses of the prior art are capable of applying a non-orthogonal biaxial loading. Prior art methods typically employ two or more separate actuators in complex test fixtures and/or pressurization techniques to apply a biaxial load to a test specimen. A disadvantage of these methods is the need for two or more loading devices and the high cost of the equipment. A review of the following references reveals the disadvantages of the prior art.

In Clay, (U.S. Pat. No. 5,905,205), an in-plane biaxial test apparatus is disclosed which comprises linkages to transfer a load to the orthogonal direction of the loading. In the reference, a rhombus-shaped four-bar linkage is attached at one vertex to a fixed attachment point and a uniaxial tensile force is applied to the opposite vertex. The test specimen is placed inside the linkage and is attached to the linkage by load transfer members connected at one end to the links of the linkage and at their other end to grips holding the test specimen. Load transfer members parallel to the applied uniaxial tensile force are attached to test specimen grips adjacent to the link attachment points of the load transfer members and perpendicular load transfer members are attached to test specimen grips opposite their link attachment points. Application of a uniaxial tensile force produces a biaxial tensile force in the test specimen. A disadvantage of the test apparatus is that it is not capable of applying in-plane shear to the test specimen. Another disadvantage is that the biaxial loading is limited to an orthogonal configuration.

In Tucchio, (U.S. Pat. No. 5,448,918), an apparatus with an X-shape is disclosed which is only used for compression load. The compression testing device is formed by two modified beams joined to form an X-shape with the support structure, such as webs and upper flanges, removed in the region of the X intersection, thereby leaving a rectangular opening. The rectangular opening has dimensions slightly greater than the widths of the beams and is open from the upper surfaces downward to the lower surfaces, which are joined together forming an X-configuration. This configuration has a flexing characteristic in the direction perpendicular to the plane of the joined beams. A test specimen support plate is attached to the underside of one of the upper surfaces and is located so as to slide below the opposing upper surface during flexing of the X-beam assembly. Each beam is supported by a roller pin. Additional roller pins are located on the specimen support plate between each beam upper flange and a specimen to be tested. A disadvantage of this apparatus is that these roller pins prevent any torsional load from reaching the test specimen.

In Ward et al., (U.S. Pat. No. 5,279,166), an apparatus for self-alignment of a biaxial loading device is disclosed. The apparatus is for testing the strength of specimens while maintaining a constant specimen centroid during the loading operation. The apparatus consists of a load frame and two load assemblies for imparting two independent perpendicular forces upon a test specimen. The test specimen centroid is maintained by providing elements for linear motion of the load frame relative to a fixed crosshead, and by alignment and linear motion elements of one load assembly relative to the load frame.

In Mathiak et al., (U.S. Pat. No. 5,144,844), a cruciform planar specimen for biaxial material testing is disclosed. A flat cross-shaped test piece is made of sheet metal for biaxially testing. This test piece includes a central region that defines an area of measurement. Four arms for applying loads to the central region extend from the central region along orthogonal axes. Each arm has one end integral with the central region and an opposite end with an end part for connection to a test device for the application of a test load. Tensile stresses can thus be applied to the central region along first and second orthogonal coordinate axes of the central measurement region. Slots in the load applying arms extend along the arms parallel to the first and second coordinate axes from the end part as far as and up to the area of measurement.

In Vanderlakis et al., (U.S. Pat. No. 4,885,941), an apparatus for compressive loading of geo-materials is disclosed. The test apparatus for geomaterial (soil, etc.) samples is designed to allow free shear band formation and provide measurements of the stress displacement characteristics of the failure zone. A geomaterial sample formed into a specimen comprising a right rectangular prism is surrounded by a thin rubber membrane and is supported by walls along two parallel faces. An axial load is kinematically applied by a plate that is guided to prevent any tilt or eccentricity, while a bottom support plate for the specimen is horizontally guided by a linear bearing that is substantially friction free. The assembly of the specimen and its supports is placed in a conventional tri-axial cell in a loading frame so that an axial load can be applied to one end of the specimen and reacted against the bottom plate. Internal loaded load cells allow for measurement of the axial force as well as friction along the side walls. Displacement transducers monitor the axial and lateral displacements of the specimen and the horizontal movement of the bottom plate.

In Holt, (U.S. Pat. No. 4,192,194), an apparatus for biaxially loading a specimen through pressurizing the inside surface of a cylinder is disclosed. A thin-wall tube specimen is biaxially tested for stress analysis by applying compressive axial stress and either internal surface pressure or external surface pressure to the specimen. Torsion is not required. The sample is positioned between platens, which are assembled inside a pressure collet. Axial compressive stress is applied through the platens to the specimen, and hydraulic pressure is applied through the assembly to the internal and external cylindrical surfaces of the specimen. The disadvantages of this art include the requirement of cylindrical shape of the specimen and the high cost and added equipment of pressurization.

In Lynch (U.S. Pat. No. 3,776,028), an apparatus requiring three independent loading mechanisms is disclosed. A three-axis, adjustable loading structure is provided for test equipment wherein it is desired to exert pressure against the structure, which is to be tested. The device of the present invention is provided with three electric drives whereby the wall angle, horizontal position, and vertical position of the test device can be positioned.

None of the above-mentioned devices and apparatuses of the cited references are capable of combining the in-plane and compression/tension loading of a test specimen while using only one loading system.

In the commonly-assigned reference, Cavallaro et al. (U.S. Pat. No. 6,860,156), a test apparatus is disclosed. The apparatus is capable of simultaneously or independently applying in-plane biaxial and shear loading to a test specimen. However, in the apparatus, the loading is applied to the test specimen by way of equal biaxial extension (or contraction).

An improvement for some material testing is where the actual applied load, not the displacement, can be controlled and applied to the test specimen. Also, in creep testing material testing of composites, anisotropic and fabrics, the tension or compression forces on the test specimen could be kept constant. By controlled loading, the axes in the plane of the specimen could be subjected to varying tension or compression, (i.e. one axis having a different loading mode than another axis). The apparatus could be easily accommodated in a conventional material testing machine to be cost effective.

SUMMARY OF THE INVENTION

Accordingly, it is an object of the present invention to provide a testing apparatus capable of applying controllable loading forces to be measured for a test specimen.

A further object of the present invention is to provide a testing apparatus capable of having a different loading mode in each axis of the plane of the test specimen; that is, tension loading in one axis and compression loading in another axis.

A still further object of the present invention is to provide a testing apparatus for in-plane shear and compression and/or tensional testing of orthotropic and anisotropic materials, such as composite materials, fabrics, etc, in a creep testing situation and other testing situations.

A still further object of the present invention is to provide a testing apparatus capable of applying non-orthogonal controllable biaxial forces or equal biaxial displacements.

To attain the objects described, the present invention improves the apparatus of the Cavallaro reference and therefore the known art wherein a tensile or compressive load of a test apparatus can be converted to an unequal, orthogonal or oblique stress state on a planar test specimen by the use of two and/or four load plate assemblies and a controllable fluid pressure system. Six load plate assemblies for a tri-axial loading may also be employed with the controllable fluid pressure system.

The present invention provides flexibility in optionally applying controlled biaxial tension/compression loading forces to the test specimen by choosing different settings on adjustable check valves of the fluid pressure system acting as control devices and shutoff valve acting as directional fluid conduits. An in-plane shear load can be applied either simultaneously or independently of the biaxial tension/compression load.

The test apparatus generally comprises two rhombus-shaped four-bar linkages that are pivotally connected to one another at superior (top) and inferior (bottom) joints through two sleeves of each joint. The two superior sleeves are axially connected to one another through a pin and two thrust bearings, so that the two sleeves can rotate freely with respect to one another while connected in the axial (vertical) direction. A similar connection is employed for the inferior sleeve.

Four loading plate assemblies are pivotally attached with a yoke to each of the lateral vertices of each of the linkages. Each loading plate assembly includes the yoke, a frame slidable to the yoke, a piston actuator and a test specimen clamp.

The actuator is a piston and cylinder arrangement fluidly connected to two pressure conduits. One conduit is connected to a chamber in front of the piston, and another conduit is connected to a chamber in rear of the piston. Shut-off valves and adjustable check valves are provided for each conduit, and a reservoir is provided for each of the two corresponding sides of the four-bar linkages.

To test a planar specimen, each end (two ends for uniaxial loading; four ends for biaxial loading, six ends for tri-axial loading etc.) of the test specimen is rigidly attached to the clamp of each loading plate assembly. The superior and inferior joints are also attached to the top and the bottom crosshead of a conventional testing machine.

Upon downward movement of the superior vertices, the lateral vertices extend outwardly; thereby, separating the two corresponding loading plate assemblies from each other. This action applies tension on the test specimen. Likewise, upon upward movement of the superior vertices of the rhombuses, the lateral vertices contract inwardly; thereby, moving the two corresponding loading plate assemblies to each other. This movement applies compression to the test specimen.

The magnitude of the applied biaxial forces on the test specimen is controllable through adjustable check valves controlling fluid pressure to the piston actuator to control movement of the yoke and frame in relation to each other thereby impacting loading of the test specimen.

In an alternate loading for material testing, by rotating one linkage with respect to the other, the test specimen will be subjected to in-plane shear.

BRIEF DESCRIPTION OF THE DRAWINGS

Thus by the present invention its objects and advantages will become readily apparent upon reading the following detailed description taken in conjunction with the accompanying drawings, in which.

DESCRIPTION OF THE PREFERRED EMBODIMENT

Figure 1:
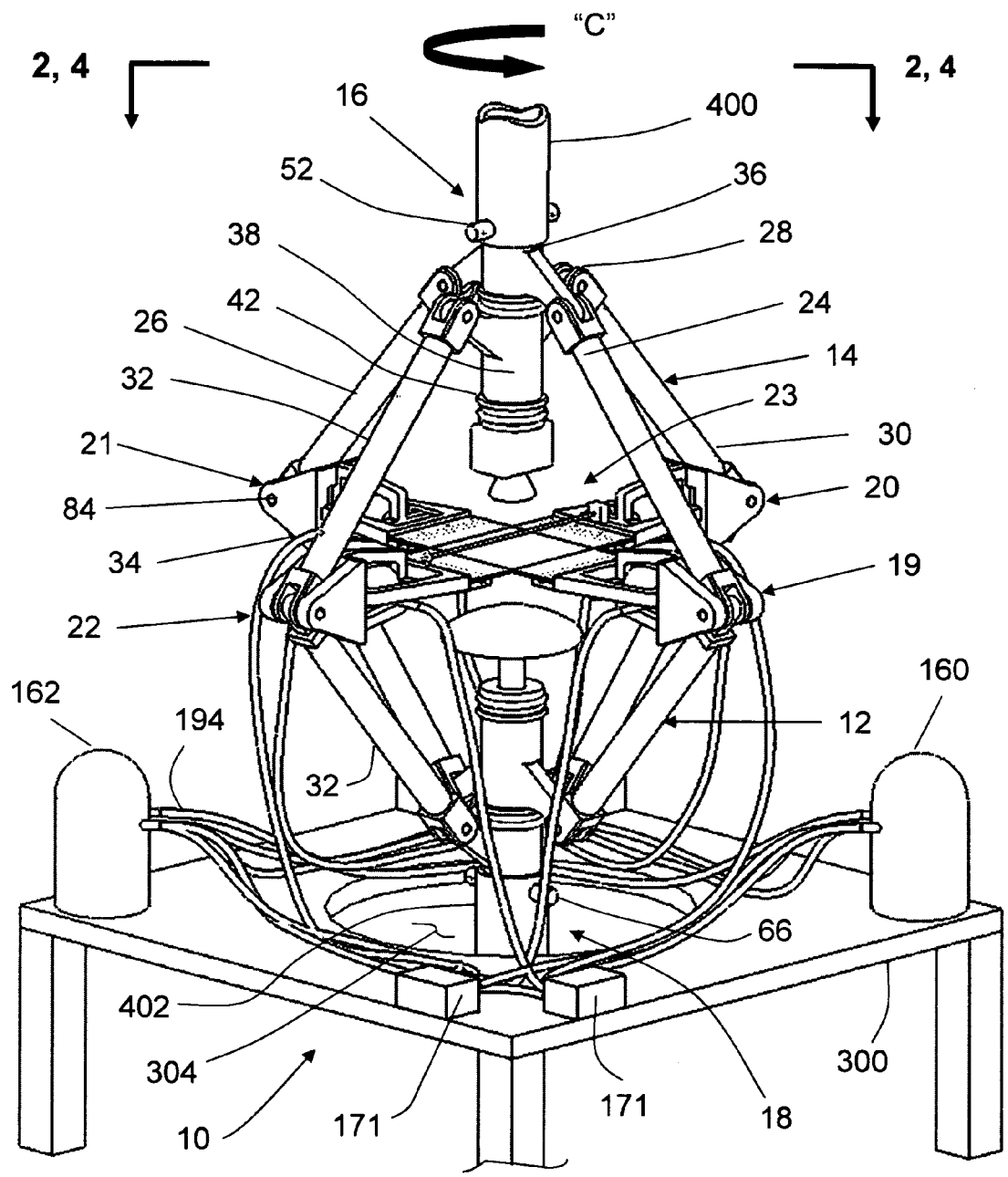
FIG. 1 is a perspective view of the testing apparatus of the present invention with loading plate assemblies of the apparatus shown clamped to a test specimen.
Figure 2:
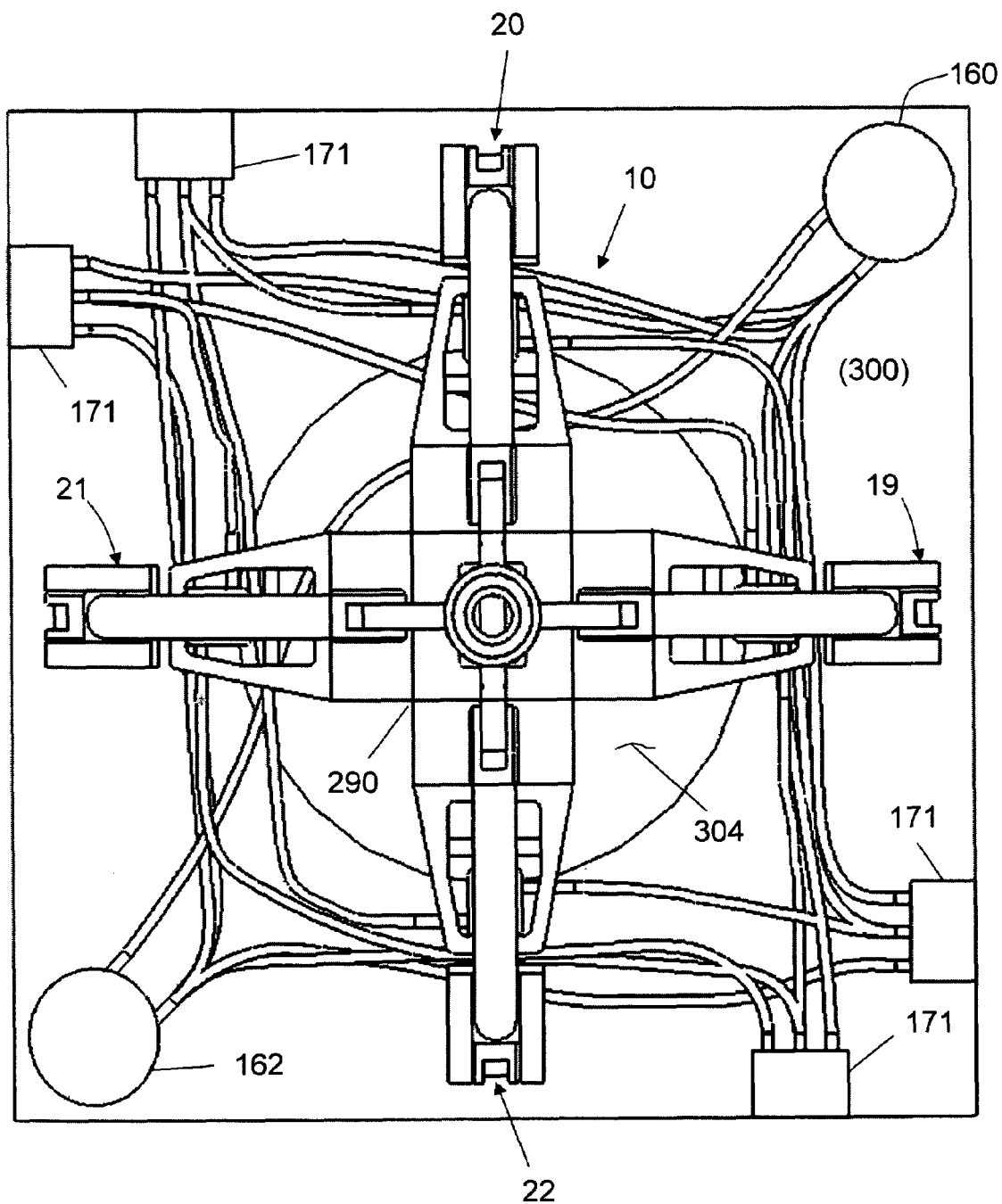
FIG. 2 is a plan view of the testing apparatus of the present invention with the view taken from reference line 2—2 of FIG. 1.

Referring now to the drawings wherein like numerals refer to like elements throughout the several views, one sees that FIGS. 1–5 depict an embodiment of the biaxial testing apparatus 10 (hereinafter known as the apparatus) of the present invention.

The apparatus 10 generally comprises two rhombus-shaped four-bar linkages 12 and 14, a superior (top) joint 16, an inferior (bottom) joint 18, loading plate assemblies 19, 20, 21, 22 and a strain/displacement measurement system 23.

The linkage 12 includes two pairs of link bars 24 and 26, extending from the superior joint 16 to the inferior joint 18. Ends of each link bar are rigidly connected to brackets 28 that pivotally connect to the superior joint 16 and the inferior joint 18. Similarly, the linkage 14 includes two pairs of link bars 30 and 32, extending from the superior joint 16 to the inferior joint 18. The ends of each link bar are rigidly connected to the brackets 28 that pivotally connect to the superior joint 16 and the inferior joint 18. The link bars of linkages 12 and 14 are joined to each other through a lateral joint 34. The lateral joints 34 pivotally connect pivotally with the loading plate assemblies 19, 20, 21 and 22.

Figure 6:
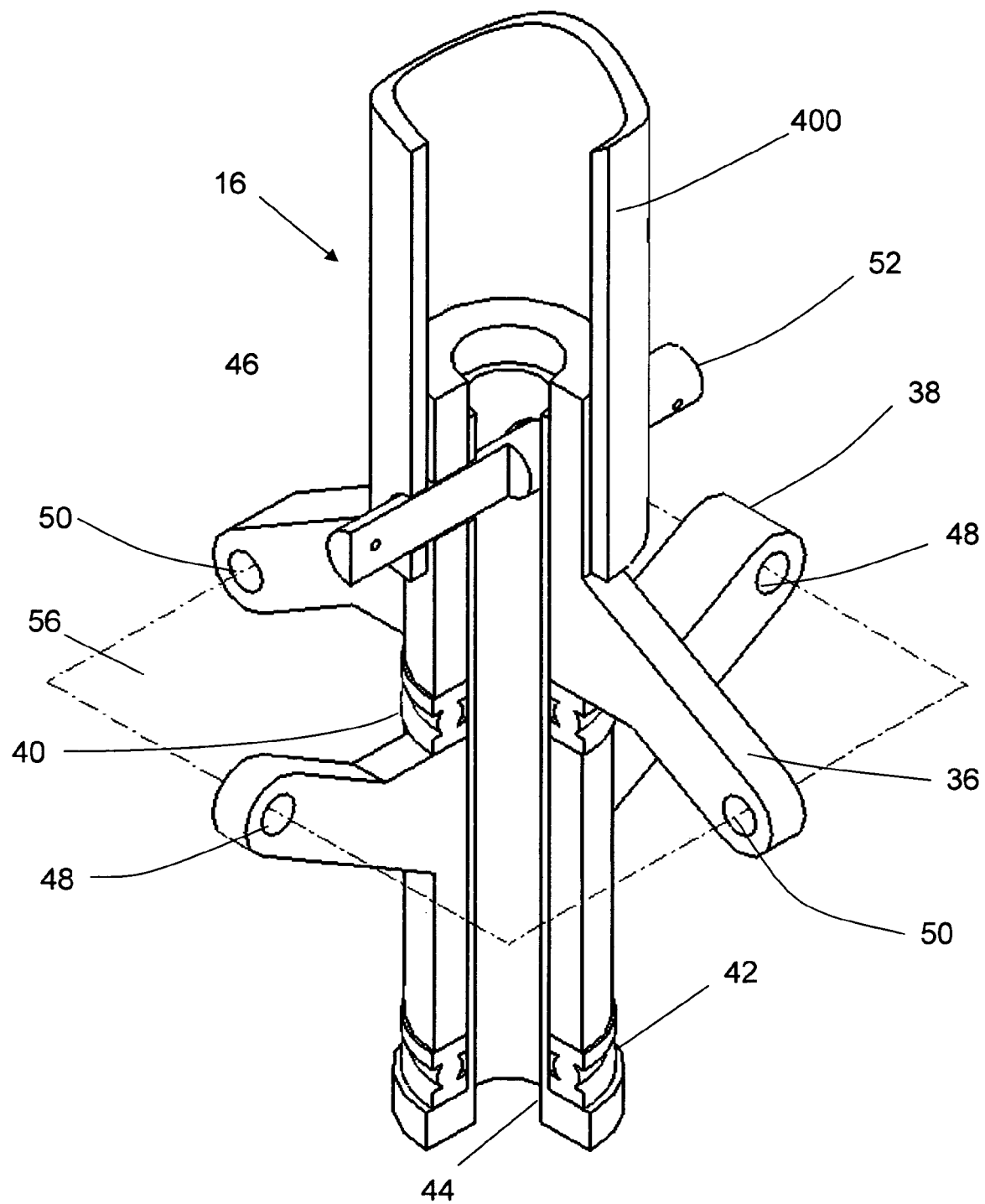
FIG. 6 is a cross-sectional view of the superior joint of the testing apparatus with the view depicting sleeve components of the superior joint.

Referring to FIG. 6, the superior joint 16 includes a top sleeve 36, a bottom sleeve 38, a top thrust bearing 40, a bottom thrust bearing 42, a connecting rod 44 and an aperture 46. The bottom sleeve 38 has two apertures 48 at the distal end of extending arms of the sleeve that are 180 degrees apart from one another. Similarly, the top sleeve 36 has two apertures 50 at the distal end of extending arms of the top sleeve that are 180 degrees apart from one another.

A pin 52, which passes through the aperture 46, rotatably connects the top sleeve 36 and the bottom sleeve 38 to a crosshead 400 of a testing machine (not completely shown). The pin 52 restrains the vertical motion of the bottom sleeve 38 and the top sleeve 36, and yet allows rotation of one sleeve with respect to the other. The link bars 30 and 32 of the linkage 14 are pivotally connected to the bottom sleeve 38 through the two apertures 48. Likewise, the link bars 24 and 26 of the linkage 12 are pivotally connected to the top sleeve 36 through the apertures 50.

For an equi-biaxial displacement loading, the height of the apertures 48 and 50 of the superior joint 16 are located on a phantom horizontal plane 56. This is the reason that the bottom sleeve 38 has upward extending arms and the top sleeve 36 has downward extending arms.

Figure 3:
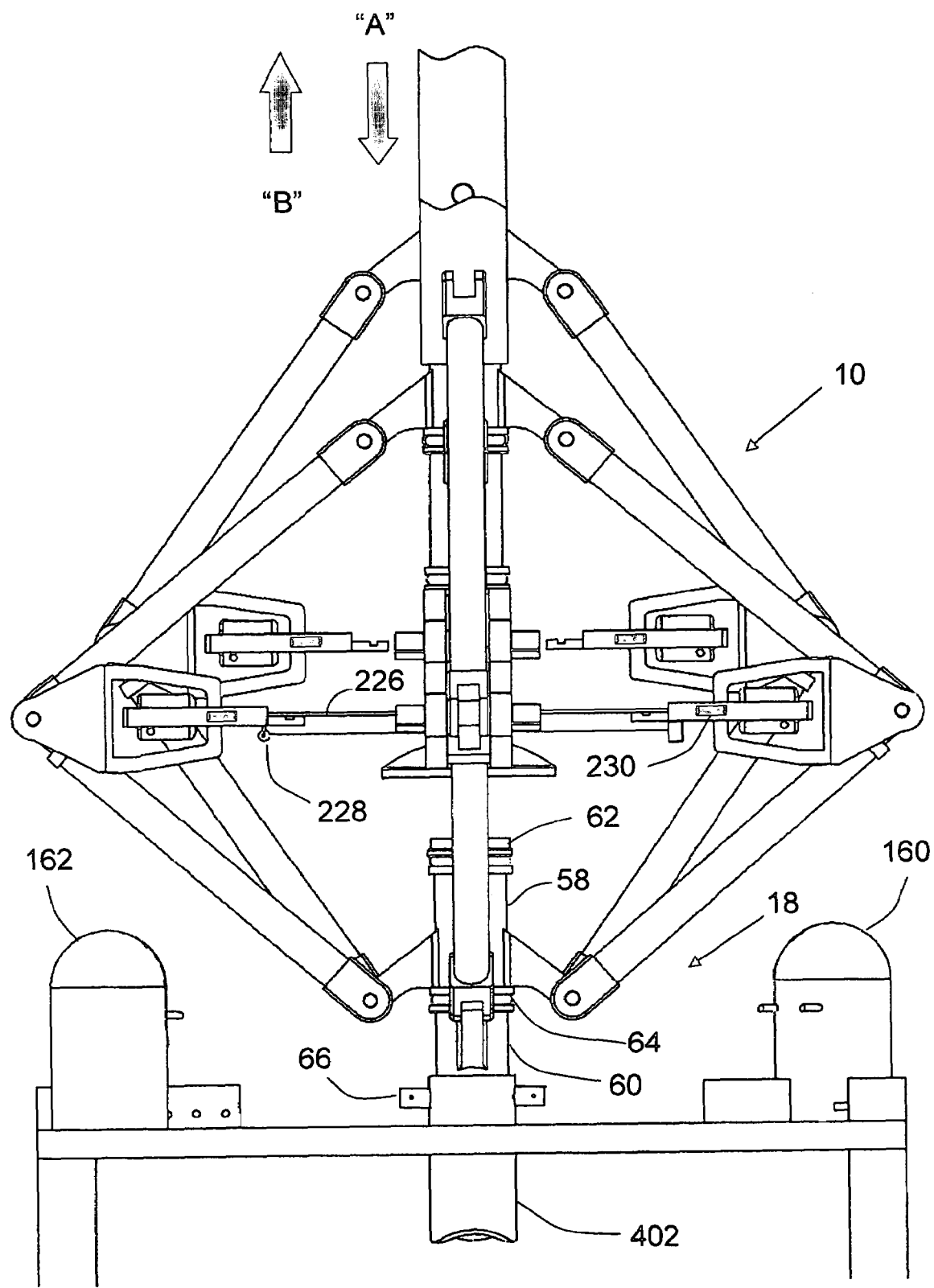
FIG. 3 is a side view of the testing apparatus of the present invention with tension and compression loading by the apparatus shown and with the fluid conduits removed for clarity of the view.
Figure 4:
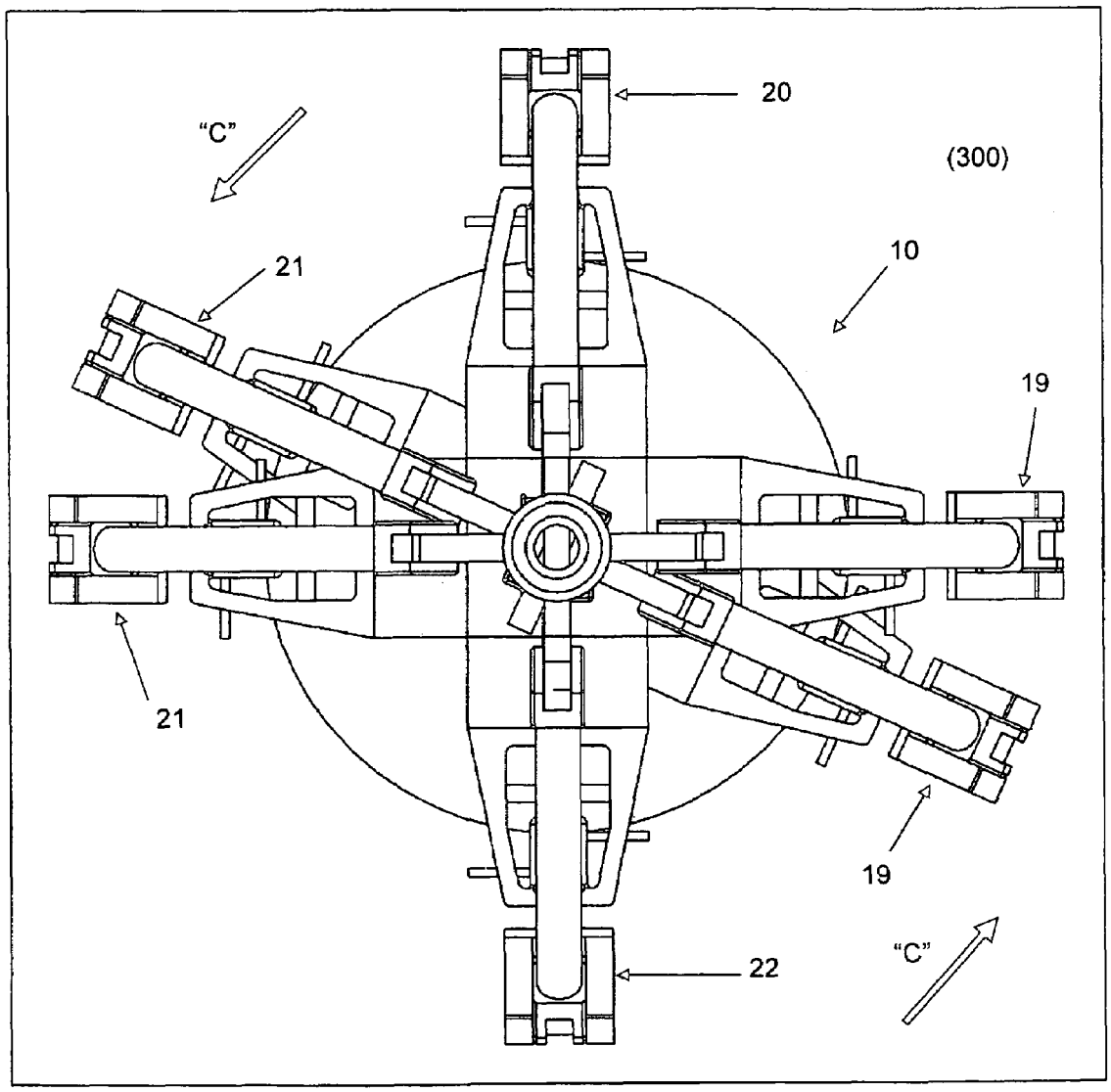
FIG. 4 is a top view of the testing apparatus of FIG. 1, when the test specimen is subjected to in-plane shear and with the view depicting twenty degrees of rotation of one of the linkages with respect to another linkage.

Referring to FIG. 3, the inferior joint 18 includes a top sleeve 58, a bottom sleeve 60, a top thrust bearing 62, a bottom thrust bearing 64 and a pin 66. Similar to the superior joint 16, the sleeves of the inferior joint 18 are rotatably connected to one another through the pin 66. That is, the top sleeve 58 and the bottom sleeve 60 are restrained to rotation along the vertical axis of the apparatus 10. A crosshead 402 of the testing machine is rigidly connected to the inferior joint 18 through the pin 66.

Figure 7:
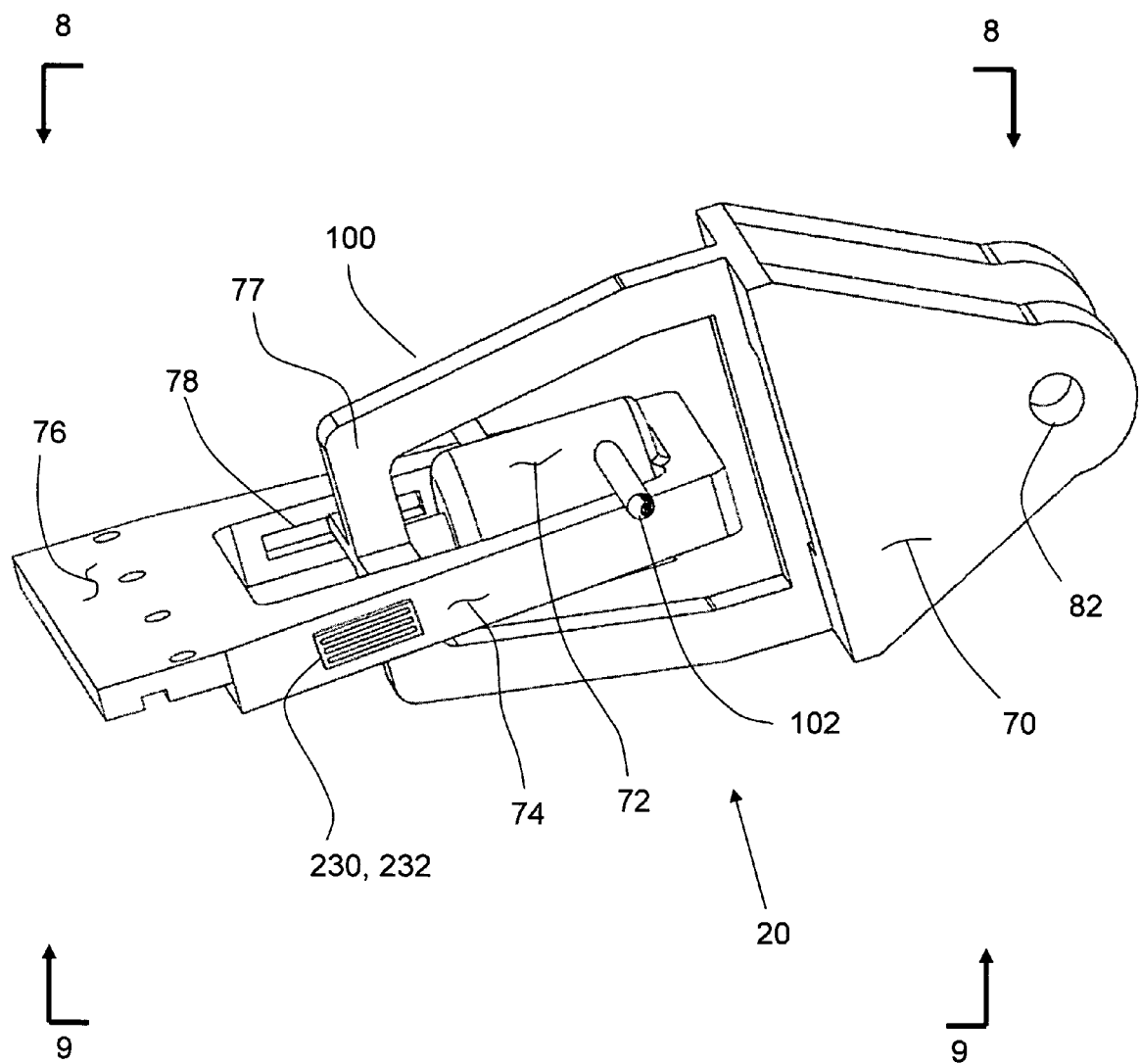
FIG. 7 is a perspective view of a loading plate assembly of the testing apparatus of the present invention.

Referring to FIG. 7, the loading plate assembly 20 of the apparatus 10 (loading plate assemblies 19, 21 and 22 have similar construction) includes a yoke 70, a piston actuator 72, a frame 74 and clamp attachment 76.

The yoke 70 has a pair of stabilizer arms 77 extending from a longitudinal axis of the yoke to slidably move within slots 78 of the surrounding frame 74. As will be described further, the stabilizer arms 77 provide control for compression and tension loading of a test specimen 290. The stabilizer arm 77 also reduces relative rotations and stabilizes motion within the loading plate assembly 20. The yoke 70 has two apertures 82 to pivotally connect the yoke to the lateral joint 34 by rotation on a pin 84 (see FIG. 1).

Figure 8:
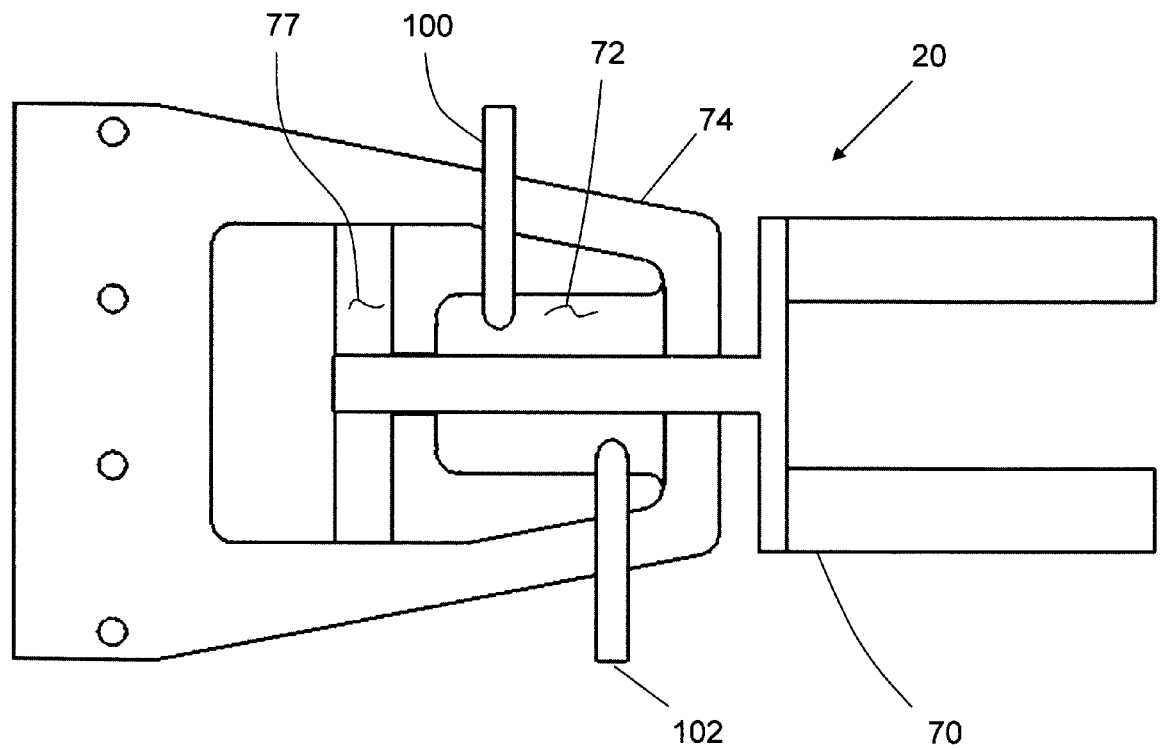
FIG. 8 is a plan view of the loading plate assembly with the view taken from reference line 8—8 of FIG. 7.
Figure 9:
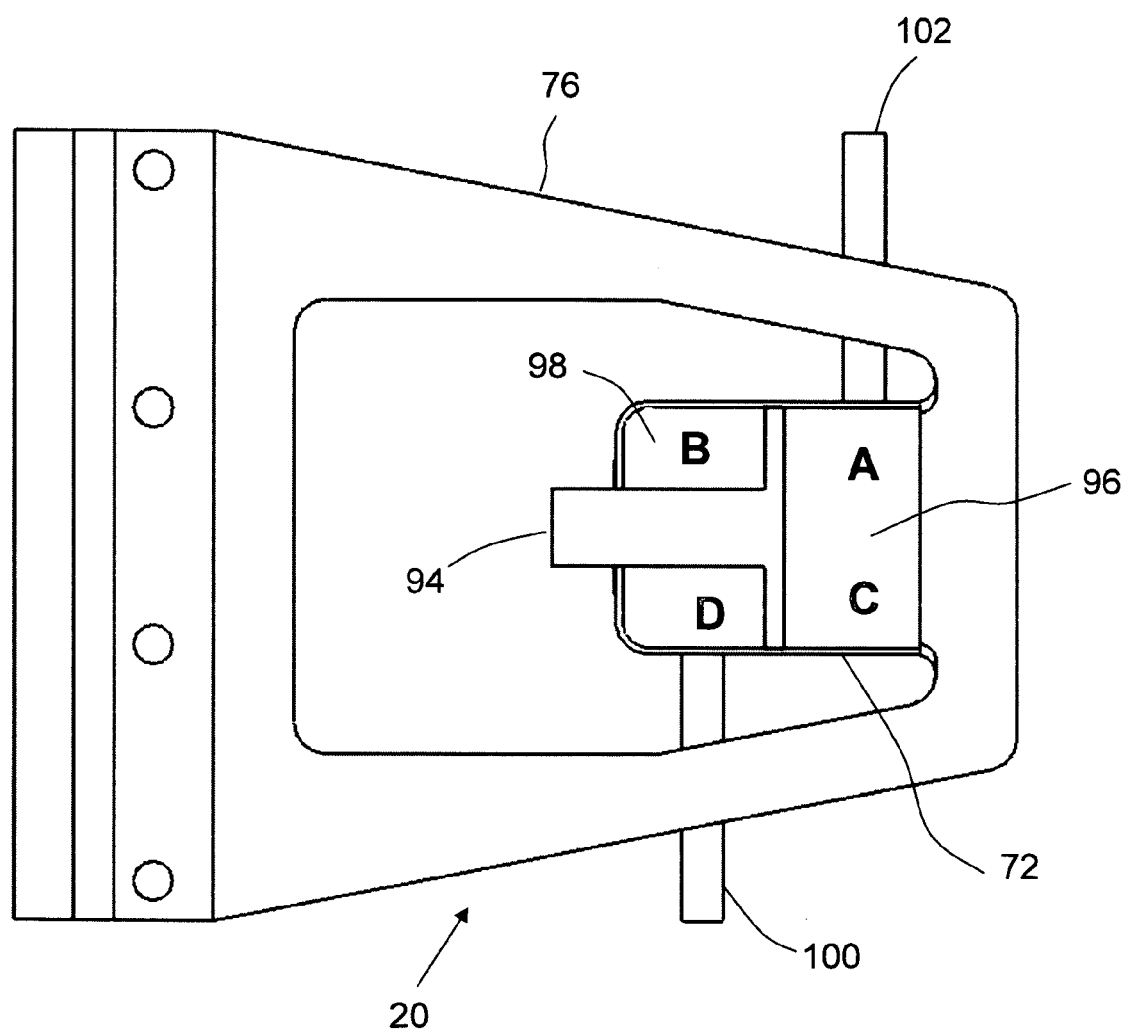
FIG. 9 is a cross-sectional view of a frame and piston actuator of the loading plate assembly with the view taken from reference line 9—9 of FIG. 7.

Referring to FIGS. 8 and 9, the actuator 72 encompasses a piston 94, and a chamber 96 adjacent to the piston (for operations designated to chambers A or C) and a chamber 98 on the opposite side of the piston (for operations designated to chambers B and D). Two pressure connections 100 and 102 for pressure lines are fluidly connected to opposite sides of the piston 94 to pressure or release pressure from the chambers 96 and 98 by movement of high and/or low-pressure fluid to and from the chambers. The chambers 96 and 98 are capable of filling with a fluid (if hydraulic) or gas (if pneumatic).

Figure 10:
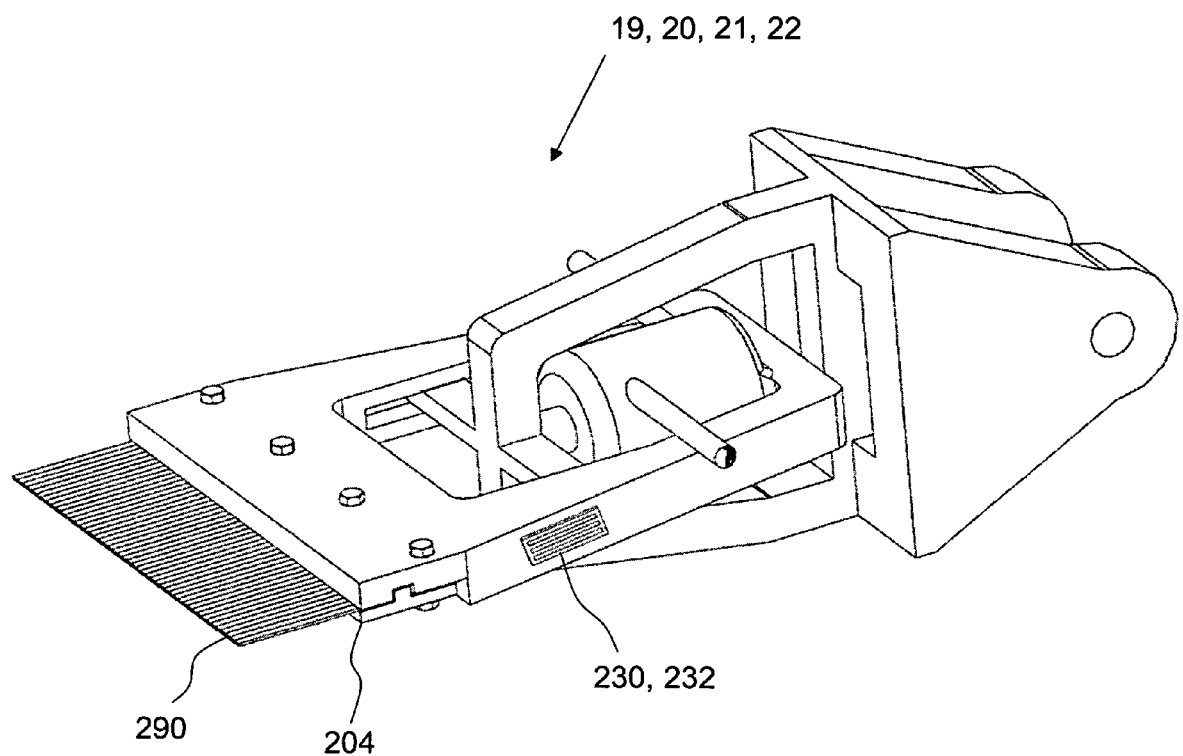
FIG. 10 is a perspective view of a clamping mechanism of the loading plate assembly.
Figure 11:
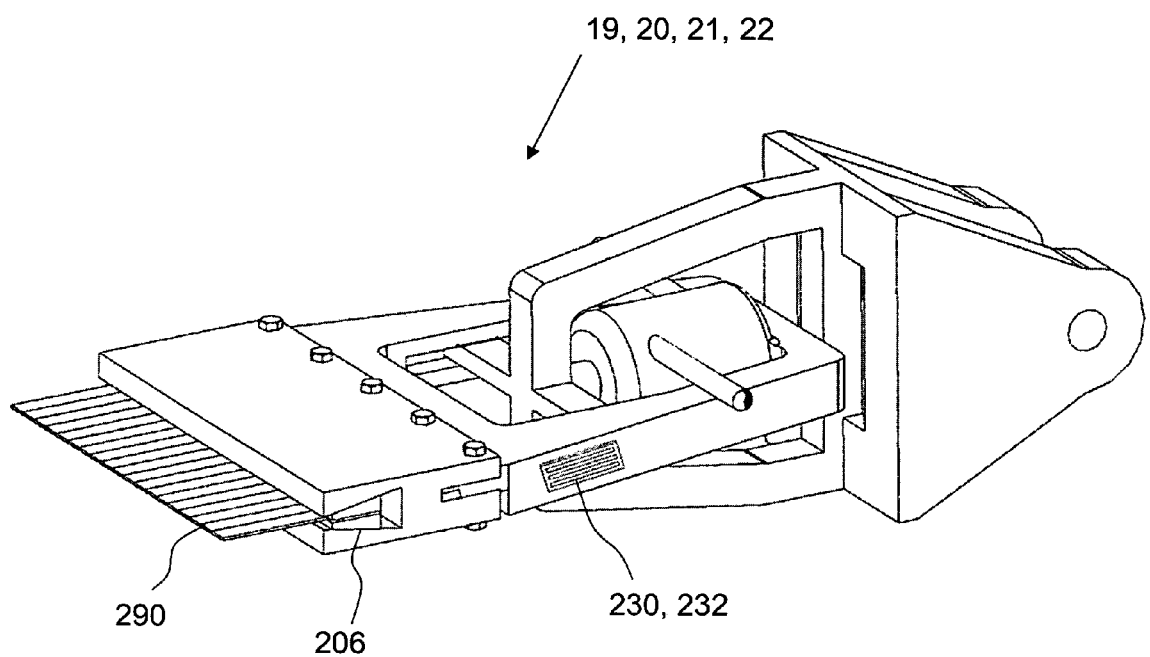
FIG. 11 is a perspective view of an alternate clamping mechanism of the loading plate assembly.
Figure 12:
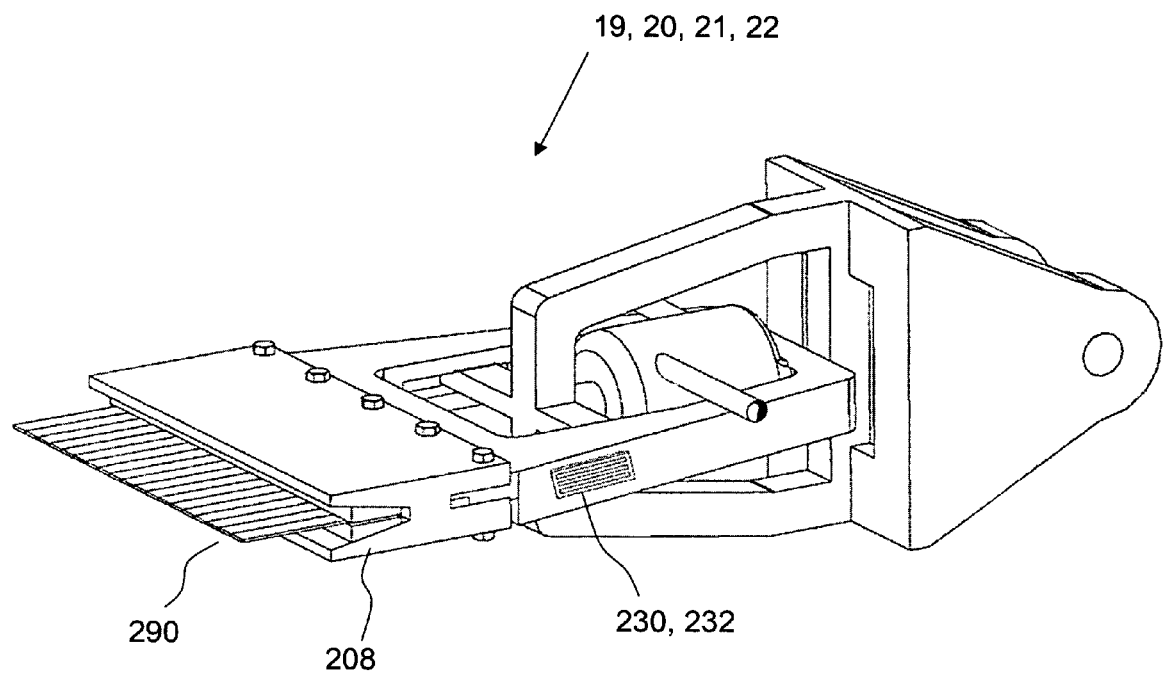
FIG. 12 is a perspective view of a second alternate clamping mechanism of the loading plate assembly.

Each loading plate assembly 19, 20, 21 and 22 has a conventional clamping mechanism, a tongue and groove clamp 204 (as shown in FIG. 10) a wedge clamp 206 for tensile loading (as shown in FIG. 11) or a compressive wedge clamp 208 for compressive loading (as shown in FIG. 12). These clamps are rigidly attached by connection to each of end of a test specimen 290 (typically four ends if for biaxial loading, two ends if for uniaxial loading, six ends if for tri-axial loading etc.).

Figure 13:
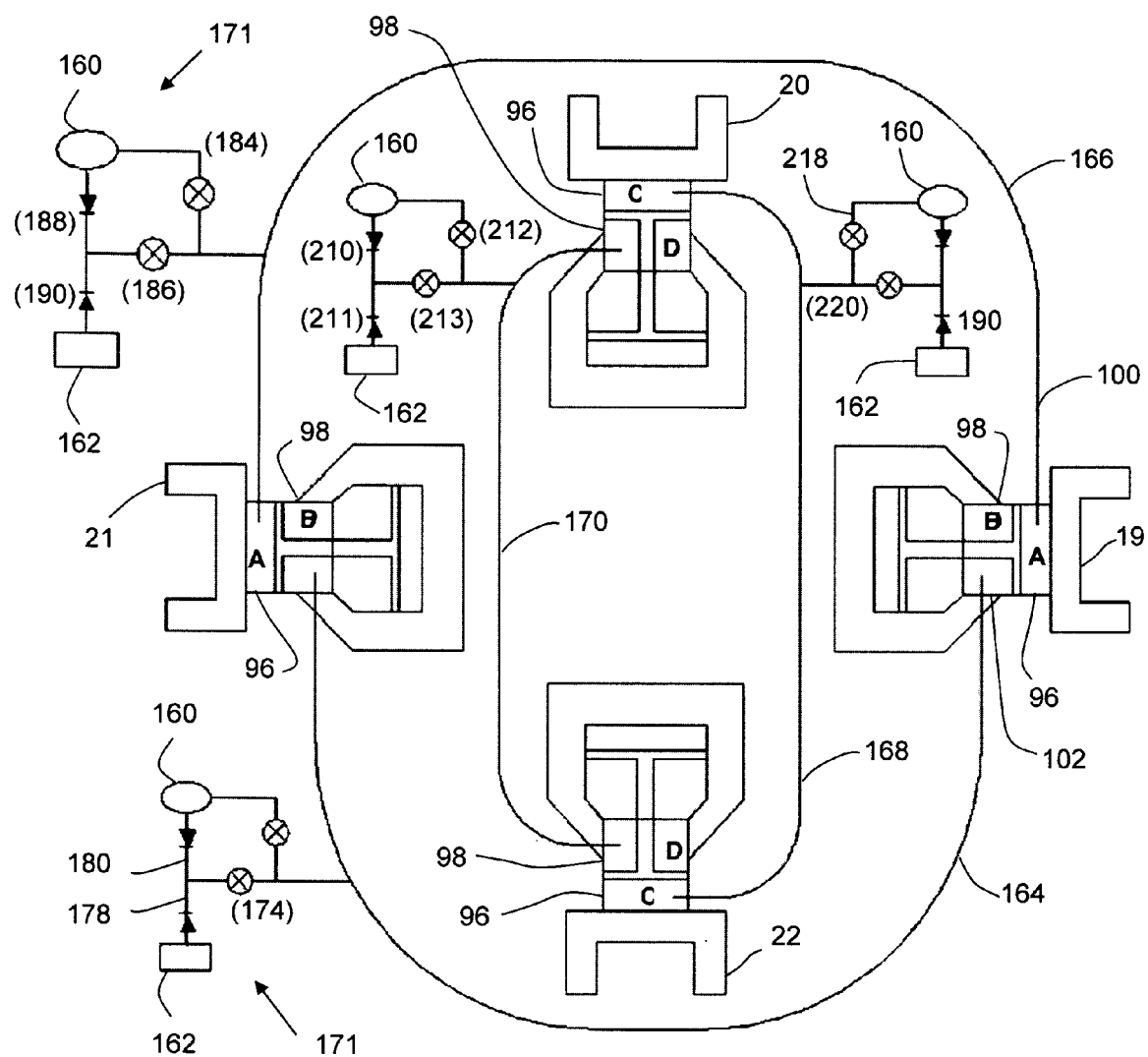
FIG. 13 is a schematic of the fluid conduits of the testing apparatus of the present invention.
Figure 14:
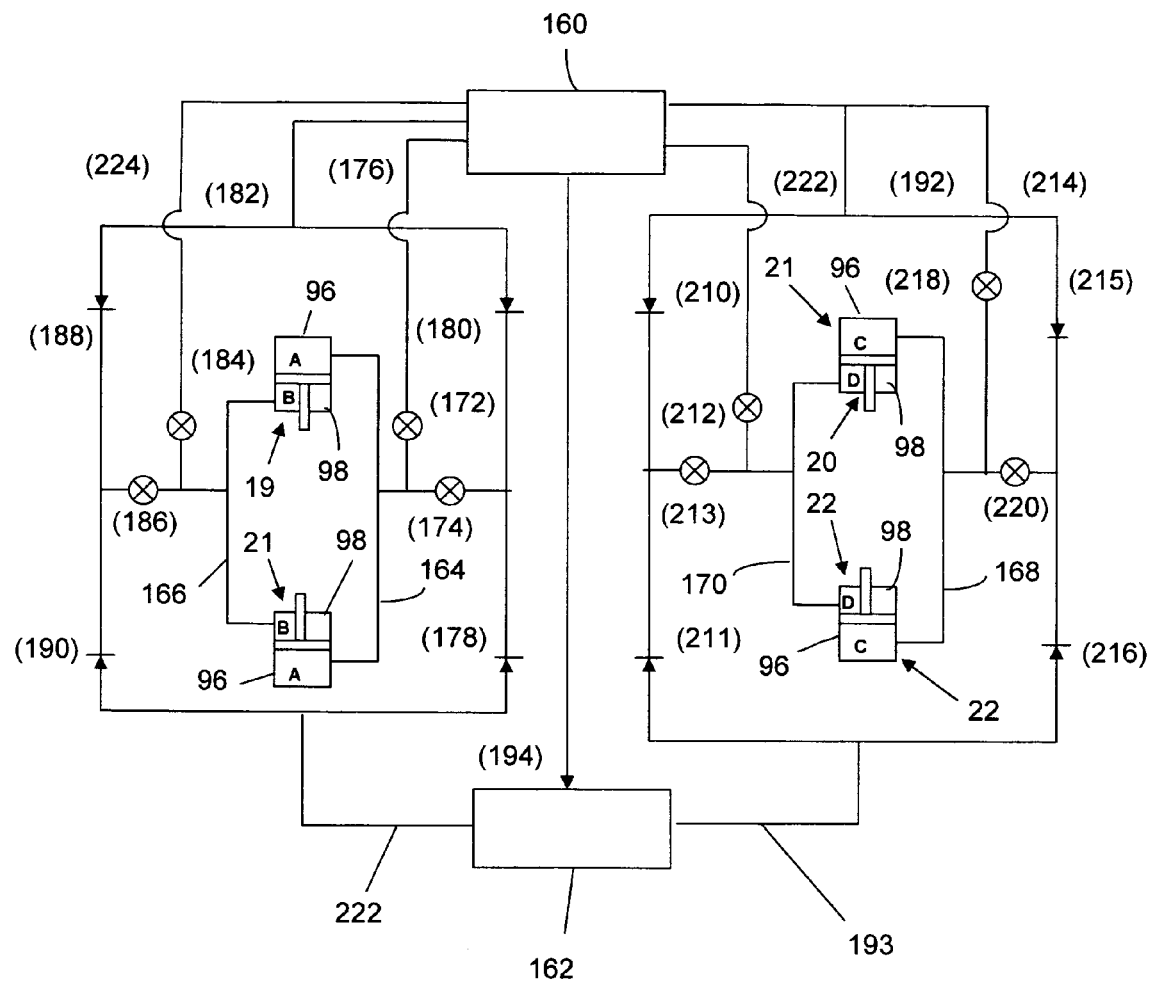
FIG. 14 is a schematic of the fluid conduits related to a symmetric loading with the loading plate assembly.
Figure 15:
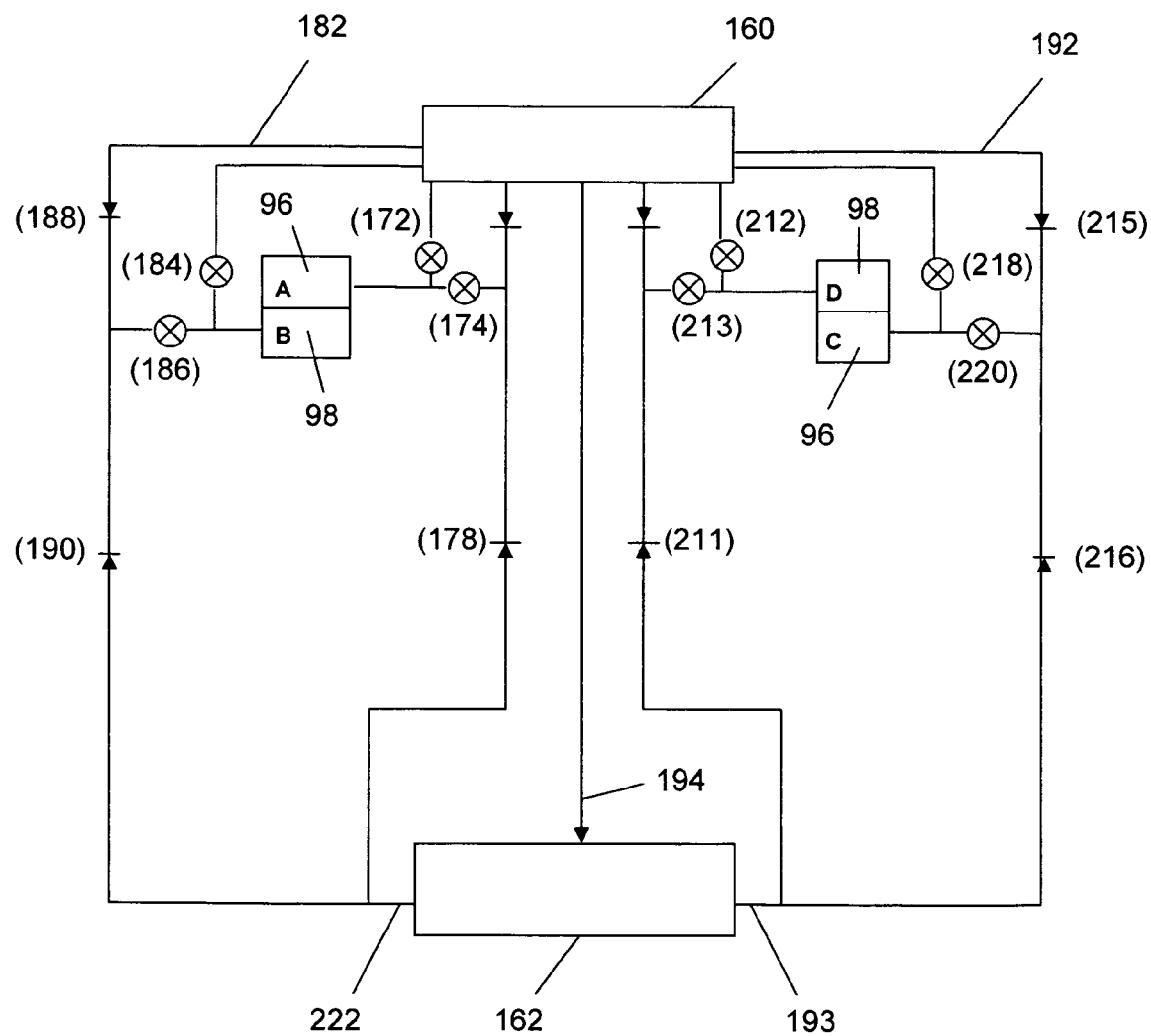
FIG. 15 is a schematic of the fluid conduits related to an asymmetric loading with the loading plate assembly.

Referring to the pressure control function depicted in FIGS. 13–15, the pressure connections 100 and 102 (shown for loading assembly 19 and similar for assemblies 20, 21 and 22) are fluidly connected by conduits to a reservoir 160 and a pressure source 162, such as a pump. There are several of the conduits that fluidly connect the chambers A, B, C and D of the piston actuators 72 of the loading assemblies. Conduits 166 and 164 fluidly connect chambers 96 (A) and 98 (B) of the loading plate assemblies 19 and 21. Similarly, conduits 170 and 168 fluidly connect chambers 96 (C) and 98 (D) of the loading plate assemblies 20 and 22. Each conduit is connected to a controller 171. Each controller 171 includes shut-off valves and adjustable check valves (detailed below) that are connected to the reservoir 160 and the pump 162. The reservoir 160 and the pump 162 are shown repetitively throughout FIG. 13 to illustrate the loop connectivity of the pressure system of the apparatus 10. The preferred pressure system employs one pump 162 and one reservoir as shown in FIG. 1, FIG. 2, FIG. 3, FIG. 14 and FIG. 15.

Referring to FIG. 14, for the pressure-controlled operation of loading plate assemblies 19 and 21, the conduit 164 is fluidly connected to shutoff valves 172 and 174, whereupon opening the shutoff valve 172 and closing the shutoff valve 174, the conduit 164 is fluidly connected to the reservoir 160 through conduit 176. This operation allows the pressure in the chamber 96 (A) to release to the reservoir 160. When the shutoff valve 172 is closed and the shutoff valve 174 is opened, the conduit 164 is fluidly connected to adjustable check valves 178 and 180 and the fluid pressure of the pump 162.

In an alternate operation, when the valve 174 is opened and the valve 172 is closed, the adjustable check valve 180 opens and releases the pressure to the reservoir 160 through conduit 182 when the pressure in the chamber 96 (A) exceeds a preset value. On the other hand, the adjustable check valve 178 opens and pressurizes into the chamber 96 (A) from the pump 162, when the pressure in the chamber drops a preset value. Likewise, when shutoff valve 184 is closed and shutoff valve 186 is opened, adjustable check valve 188 opens and releases the pressure to the reservoir 160 through the conduit 182 when the pressure in the chamber 98 (B) exceeds a preset value. Alternatively, adjustable check valve 190 opens and pressurizes the chamber 98 (B) from the pump 162, when the pressure in the chamber drops a preset value.

The pressure system for the two loading plate assemblies 20 and 22, shown on the right side of FIG. 14 is similar to the above-described hydraulics for the loading plate assemblies 19 and 21. For example, when the valve 220 is opened and the valve 218 is closed, the adjustable check valve 215 opens and releases the pressure to the reservoir 160 through conduit 222 when the pressure in the chamber 96 (C) exceeds a preset value. On the other hand, the adjustable check valve 216 opens and pressurizes into the chamber 96 (C) from the pump 162, when the pressure in the chamber drops a preset value. Likewise, when shutoff valve 212 is closed and shutoff valve 213 is opened, adjustable check valve 210 opens and releases the pressure to the reservoir 160 through conduit 192 when the pressure in the chamber 98 (C) exceeds a preset value. Alternatively, adjustable check valve 211 opens and pressurizes the chamber 98 (D) from the pump 162, when the pressure in the chamber drops a preset value.

The low fluid pressure of the conduits 168 and 170 is drained to the reservoir 160 through the conduit 192 and the high-pressure fluid of the pump 162 is fed into the conduits 222 and 214 through conduit 193. The reservoir 160 supplies the fluid for the pump 162 directly through conduit 194. The pressure system is a closed system; however, fluid makeup connections known to those skilled in the art may be added to the system.

The controllers 171, the conduits for fluid movement, the reservoir 160 and the pump 162 are optimally placed on a table 300 (see FIGS. 1–4). The table 300 has an aperture 304 for the crosshead 402 of the testing machine to operate the testing apparatus 10.

The pressure-controlled system applies a symmetric loading on the test specimen 290, since the tension or compression loads are applied simultaneously to opposing ends of the test specimen with pairs of the corresponding loading plate assemblies 19 and 21 or with the loading plate assemblies 20 and 22. This feature is important if the geometric center of the test specimen 290 needs to be centered in the testing apparatus 10.

The pressure system may not apply a symmetric loading, that is, the tension or compression can be applied at one of the loading plate assemblies in each direction. Therefore, in another embodiment, the pressure system may be connected only to one set of the loading plate assemblies, such as the loading plates assemblies 19 and 20. The flow pattern and arrangement of the shutoff valves and the adjustable check valves of the asymmetric embodiment are shown in FIG. 15, which is schematically similar to FIG. 14.

Referring to FIG. 1 and FIG. 3, operation of the test apparatus 10 involves first connecting the test apparatus to the crossheads 400 and 402 of the testing machine with the pins 52 and 66. For biaxial loading, the four sides of the test specimen 290 are rigidly connected to the clamps of the loading plate assemblies 19, 20, 21 and 22. For tensile loading of planar solids, the wedge clamp 206 is used. The clamp 208 is used for compressive loading. The tongue and groove clamp 204 is used for fabrics. These clamps 204, 206 and 208 can be rigidly attached by the clamp attachments 76 of the loading plate assemblies 19, 20, 21 and 22.

Upon downward movement of the crosshead 400 in direction "A", the lateral joints 34 move outward and separate from one another; thereby, converting the compressive vertical load of the crosshead into a biaxial tension in the plane of the test specimen 290. The transformation of the load from the vertical direction to the planar biaxial direction is achieved by compressive load of the link bars 24, 26, 30 and 32 on the lateral joints 34.

Similarly, upward movement of the crosshead 400 in direction "B" will be converted to a biaxial compression in the plane of the test specimen 290. Upon rotation of the superior crosshead 400 in direction "C", the top sleeve 36 rotates with respect to the bottom sleeve 38, thereby rotating the linkage 12 with respect to the linkage 14. As a result, the loading plates assemblies 19, 20, 21 and 22 rotate with respect to one another and apply a shearing load to the test specimen 290. This shear occurs mainly because the crosshead 402 is fixed with respect to the frame of the test machine.

Without the pressure-controlled system, the apparatus 10 operates in a displacement-controlled mode where the actions of the testing apparatus are dependent on the movement of the crossheads 400 and 402. The operation of the testing apparatus 10 in a force controllable mode involves pressurization through the pump 162.

For subjecting the test specimen 290 to a force-controllable tensile force, the crosshead 400 of the testing machine is moved in direction "A" and the lateral hinges of the linkages 12 and 14 expand away from the longitudinal center of the testing apparatus 10. At the same moment, the chambers 96 (A) and/or (C), are pressurized through the check valves 178 and 216. That is, the shutoff valves 172 and 218 are closed and shutoff valves 174 and 220 are opened. In this condition, the chambers 98 (B) and/or (D), are fluidly connected to the reservoir 160 through conduits 182 and 222 with the shutoff valves 184 and 212 open, and the shutoff valves 186 and 213 closed.

High-pressure fluid is provided by the pump 162 to the chambers 96 and 98 through the conduit 193 and conduit 222. Assuming that the test specimen 290 is subjected to a constant tensile load of k-pounds that corresponds to a set pressure of m-psi (pound per square inch); the check valves 178, 190, 211 and 216 increase the pressure accordingly to what is needed. Alternatively, the check valves 180, 188, 210 and 215 decrease the pressure as needed. For example, as the pressure in the chambers 98 (B) and (D) reaches the "m" pressure value, and if the pressure of the chamber increases beyond the "m" pressure, the check valves 188 and 210 will open.

When the test specimen 290 is to be subjected to a symmetric constant or controlled compression of L-pounds, the crossheads 400 and 402 of the testing machine are moved away from the center of the test specimen and the lateral joints 34 move closer to the center of the test specimen. At the same moment, the check valves for the chambers 96 (A) and (C) are pressurized to a pressure set of N-psi. The shutoff valves 174 and 220 are opened and the shutoff valves 186 and 213 are closed. The chambers 98 (B) and (D) are opened to the reservoir 160 via the shutoff valves 184 and 212 and the conduits 224 and 222. The compression force on the test specimen 290 increases when, through the pump 162 and the conduits 222 and 193; check valves 178 and 216 open and pressurize the chambers 96 to the specified pressure of N-psi. In the event of pressure creep (where the pressure reduces in the chambers 96), the check valves 178 and 216 will open and pressurize the chambers, thereby, keeping a constant compression load on the test specimen 290.

In the symmetric loading of the test specimen 290, as described above, the geometric center of the test specimen remains at the center of the testing apparatus 10. In a second variation of the embodiment, where there is no need for the center of the test specimen 290 and the testing apparatus 10 to align; the pressure system of FIG. 15 represents the needed action. In this variation of embodiment, only one loading plate assembly in each loading direction includes the actuator 72. The operation of the apparatus 10 in a force controllable mode involves pressurization of the source through the pump 162.

For subjecting the test specimen 290 to a constant or a controllable tensile force, the crosshead 400 of the machine is brought down and the lateral hinges of the linkages 12 and 14 expand away from the longitudinal center of the apparatus 10. At the same moment, the chambers 98 (B) and/or (D), are pressurized through the check valves 178 and 216. Situationally, the shutoff valves 172 and 218 are closed and shutoff valves 174 and 220 are opened. To prevent hydraulic lock, the chambers 96 (A) and/or (C), are fluidly connected to depressurize to the reservoir 160 with the shutoff valves 172, 218 opened and the shutoff valves 174, 220 closed.

High-pressure fluid is provided by the pump 162 to the chambers 98 (B) and (D) through the conduit 193 and conduit 222. Assuming that the test specimen 290 is subjected to a constant tensile load of k-pounds that corresponds to a set pressure of m-psi; of the adjustable check valves 190 and 211 increase the needed pressure accordingly. As the pressure in the chambers 98 (B) and (D) reaches the "m" pressure value, and if the pressure of the chamber increases beyond the "m" pressure, the check valves 188 or 210 open.

When the test specimen 290 is to be subjected to a symmetric constant or controlled compression of L-pounds, the crossheads 400 and 402 of the testing machine are moved away from the center of the test specimen and the lateral joints 34 move closer to the center of the fabric.

At the same moment, the check valves for the chambers 96 (A) and (C) are pressurized to a pressure set of N-psi. The shutoff valves 174 and 220 are opened and the shutoff valves 172 and 218 are closed. The chambers 98 (B) and (D) are opened to the reservoir 160 through the shutoff valves 184 and 212.

The compression force on the test specimen 290 begins when, through the pump 162 and the conduits 222 and 193; adjustable check valves 178 and 216 open and pressurize the chambers 96 (A) and (C) to the specified pressure of N-psi. In the event of pressure creep where the pressure reduces in the chambers 96 (A) and (C), the adjustable check valves 178 and 216 open and pressurize the chambers, thereby keeping a constant compression load on the test specimen 290.

Figure 5:
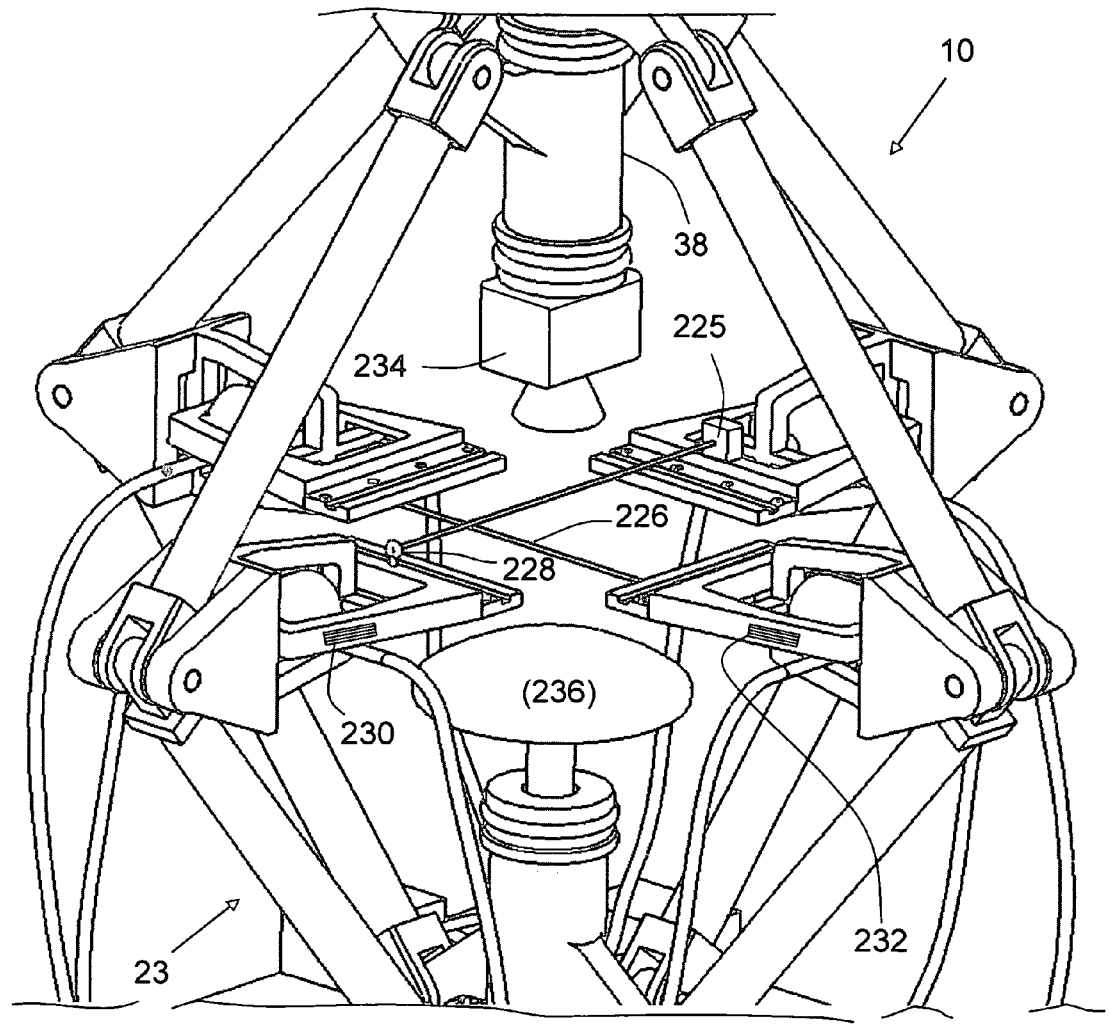
FIG. 5 is a perspective view of the testing apparatus of the present invention with the view depicting the measurement devices of the testing apparatus.

In addition to tensile or compressive load measurement through the pressure system, the conventional strain and displacement measurement system 23 is utilized to measure the biaxial displacements, rotation and strains of the test specimen 290. As shown in FIG. 5, a conventional displacement wire transducer 225, or a conventional Linear Variable Displacement Transducer (LVDT) is placed on a top surface of the loading plate assembly. Through a connecting wire or rod 226, the transducer 225 is rigidly attached to a fixed hook 228 on the loading plate assembly across the corresponding joint. For the other (orthogonal) axis the transducer 225 and the hook 228 are placed on a bottom surface of the other loading plate assembly to avoid the crossing of the two wire transducers. In addition, two strain gauges 230 and 232 are placed on the sidewalls of adjacent loading plate assemblies. The strains can be converted directly to the applied biaxial load in the test specimen 290. To visually observe and record the deformation of the specimen, a camera system 234 can be utilized that is rigidly attached to the bottom sleeve 38. In addition, a drape or puncture test mechanism 236 rigidly attached to the bottom sleeve of the inferior joint 18 could be utilized.

For an equi-biaxial force loading, the length of the link bars 24, 26, 30 and 32 are equal and the pressure settings of the adjustable check valves are the same. However, to have a non-equi biaxial force loading, one could also have different pressure release settings of the adjustable check valves or a different length of the link bars 30 and 32 of the linkage 14 from the link bars 24 and 26 of the linkage 12. The displacement relationship is easily extracted by using the Pythagorean Theorem.

An alternative mode of the invention is to use the testing apparatus 10 for a non-orthogonal (oblique) biaxial loading of the test specimen 290. This is particularly important for testing of braided fabrics and non-orthogonal composite materials. To accomplish this task the angle between the planes of the two linkages 12 and 14 is matched to the angle defined by the non-orthogonal fiber directions.

Another alternative mode of the invention is to use the testing apparatus 10 for the following loading of the test specimen 290: uniaxial tension, uniaxial compression, biaxial tension, biaxial compression, uniaxial tension with in-plane shear, uniaxial compression with in-plane shear, biaxial tension with in-plane shear, biaxial compression with in-plane shear, unequal biaxial tension with in-plane shear and unequal biaxial compression with in-plane shear.

It will be understood that many additional changes in the details, materials, steps and arrangement of parts, which have been herein described and illustrated in order to explain the nature of the invention, may be made by those skilled in the art within the principle and scope of the invention as expressed in the appended claims.

What is claimed is:

1. An apparatus for testing the material properties of a specimen, said apparatus comprising:
   a top joint movable along a longitudinal axis of said apparatus, said top joint having a first sleeve capable of rotation about the longitudinal axis with said first sleeve having at least two arms extending radially outward and longitudinally to a first end of said first sleeve, and said top joint having a second sleeve adjacent to the first end of said first sleeve, said second sleeve having at least two arms extending radially outward and longitudinally to the first end of said first sleeve;
   a bottom joint including a first sleeve having at least two arms extending radially outward and longitudinally to a first end of said first sleeve of said bottom joint and having a second sleeve adjacent to the first end, said second sleeve having at least two arms extending radially outward and longitudinally to the first end of said first sleeve of said bottom joint;
   a first linkage for enclosing the specimen, said first linkage having a first, second, third and fourth oblong bars, a first link between said first and second bars and a second link between said third and fourth bars wherein said first bar links to one arm of said first sleeve of said top joint and said third bar links to another arm of said first sleeve of said top joint and wherein said second bar links to one arm of said second sleeve of said bottom joint and said fourth bar links to another arm of said second sleeve of said bottom joint;
   a second linkage for enclosing the specimen, said second linkage having a first, second, third, and fourth oblong bars, a link between said first and second bars and a second link between said third and fourth bars wherein said first bar links to one arm of said second sleeve of said top joint and said third bar links to another arm of said second sleeve of said top joint and wherein said second bar links to one arm of said first sleeve of said bottom joint and said fourth bar links to another arm of said first sleeve of said bottom joint;
   a plurality of loading plate assemblies, each of said loading plate assemblies pivotally attached with a yoke at a first end to each of said links of said first and second linkages with said yoke including arms extending on opposite sides of a longitudinal axis of said yoke and slidable within a frame exterior to said yoke with an end of said frame extending to a clamp attachable to the test specimen such that said loading plate assemblies enclose the specimen in opposing pairs where each of said loading plate assemblies and said arms movably connected to a distal end of a piston affixed at a proximate end to said frame, wherein said arms slide within said frame to control motion of said clamp to said yoke such that a test load is imparted to the specimen; and
   a pressure system fluidly connected to impact opposite faces of said piston such that one of said opposite faces is pressurized and therefore impacts said arms for the sliding motion along the longitudinal axis of said yoke.

2. The apparatus in accordance with claim 1 wherein said pressure system comprises a controller connected to a reservoir, a fluidly connected pressurized source, a plurality of fluidly connected shutoff valves and pressure-adjustable check valves, wherein said controller controls said pressurized source and said shutoff valves to pressurize said piston to impact said arms and said clamps to move toward the longitudinal axis of said apparatus thereby applying a compression load on the test specimen.

3. The apparatus in accordance with claim 2 wherein said controller wherein said controller controls said pressurized source and said shutoff valves to pressurize said piston to impact said arms and said clamps to move away from the longitudinal axis of said apparatus, thereby, applying a tensile load on the test specimen.

4. The apparatus in accordance with claim 3 wherein movement by said top joint along the axis toward said bottom joint causes each of said links of said first and second linkages to move outward from the longitudinal axis of said apparatus and each other for applying an additional tension load on the test specimen by said plurality of loading plate assemblies;
   wherein movement by said top joint along the longitudinal axis of said apparatus away from said bottom joint causes each of said links of said first and second linkages to move inward to the longitudinal axis of said apparatus and each other for the compression loading to the specimen by said plurality of loading plate assemblies; and
   wherein rotation of said first sleeve of said top joint about the longitudinal axis of said apparatus causes the movement of said plurality of loading plate assemblies of said first linkage in reaction to the rotation of said first sleeve of said top joint for applying a torsional load on the test specimen.

5. The apparatus in accordance with claim 4 wherein said bottom joint is movable along the longitudinal axis of said apparatus and wherein movement by said bottom joint along the longitudinal axis toward said top joint causes each of said links of said first and second linkages to move outward from the longitudinal axis; and
   wherein movement by said bottom joint along the axis away from said top joint causes each of said links of said first and second linkages to move inward to the longitudinal axis and each other.

6. The apparatus in accordance with claim 5 wherein said first sleeve of said bottom joint is capable of rotation about the longitudinal axis of said apparatus and wherein rotation of said first sleeve of said bottom joint about the longitudinal axis of said apparatus causes the movement of said plurality of loading plate assemblies of said second linkage in reaction to the rotation of said first sleeve of said bottom joint for applying a torsional loading to the specimen.

7. The apparatus in accordance with claim 2 wherein movement by said top joint along the longitudinal axis of said apparatus away from said bottom joint causes each of said links of said first and second linkages to move inward to the longitudinal axis of said apparatus and each other for additional compression loading on the specimen by said plurality of loading plate assemblies;

wherein movement by said top joint along the axis toward said bottom joint causes each of said links of said first and second linkages to move outward from the longitudinal axis of said apparatus and each other for applying a tension load on the test specimen by said plurality of loading plate assemblies;

wherein rotation of said first sleeve of said top joint about the longitudinal axis of said apparatus causes the movement of said plurality of loading plate assemblies of said first linkage in reaction to the rotation of said first sleeve of said top joint for applying a torsional load on the test specimen.

8. The apparatus in accordance with claim 7 wherein said bottom joint is movable along the longitudinal axis of said apparatus and wherein movement by said bottom joint along the longitudinal axis toward said top joint causes each of said links of said first and second linkages to move outward from the longitudinal axis; and wherein movement by said bottom joint along the axis away from said top joint causes each of said links of said first and second linkages to move inward to the longitudinal axis and each other.

9. The apparatus in accordance with claim 8 wherein said first sleeve of said bottom joint is capable of rotation about the longitudinal axis of said apparatus and wherein rotation of said first sleeve of said bottom joint about the longitudinal axis of said apparatus causes the movement of said plurality of loading plate assemblies of said second linkage in reaction to the rotation of said first sleeve of said bottom joint for applying a torsional loading to the specimen.

10. The apparatus in accordance with claim 9, said apparatus further comprising an optical recording device positioned adjacent to said second sleeve of said top joint such that said optical recording device is capable of recording the deformation of the specimen during loading.

11. The apparatus in accordance with claim 10, said apparatus further comprising a draping mechanism affixed to said second sleeve of said bottom joint such that said draping mechanism is capable of draping tests of the specimen during the tension loading of the specimen.

12. An apparatus for testing the material properties of a specimen, said apparatus comprising:
a means for securing the specimen;
a means for applying a compressional load to the specimen on at least two axes of the specimen;
a means for applying a tension load to the specimen on at least two axes of the specimen;
a means for fluidly controlling the applied compressional load on at least two axes of the specimen;
a means for fluidly controlling the applied tensile load on at least two axes of the specimen;
a means for applying a torsional load to the specimen; and
a means for measuring the compressional and tensile load.

13. The apparatus in accordance with claim 12 wherein said means for applying a compressional and said means for applying the tensile load includes means for applying the compressional and tensile load at sections of the specimen in which the sections are non-orthogonal to each other.

14. The apparatus in accordance with claim 13 said apparatus further comprising means for visually recording the deformation of the specimen during the compressional, tensile and torsional load applications.

15. The apparatus in accordance with claim 14 said apparatus further comprising means for drape testing the specimen.

16. The apparatus in accordance with claim 15 said apparatus further comprising means for puncture testing the specimen.

\* \* \* \* \*